United States Patent [19]

Shmulewitz

[11] Patent Number: 5,233,994
[45] Date of Patent: Aug. 10, 1993

[54] DETECTION OF TISSUE ABNORMALITY THROUGH BLOOD PERFUSION DIFFERENTIATION

[75] Inventor: Ascher Shmulewitz, Seattle, Wash.

[73] Assignee: Advanced Technology Laboratories, Inc., Bothell, Wash.

[21] Appl. No.: 699,032

[22] Filed: May 13, 1991

[51] Int. Cl.[5] .......................... A61B 8/06; A61B 8/08
[52] U.S. Cl. ...................... 128/661.08; 128/660.02; 128/660.03; 128/24 AA
[58] Field of Search ........ 128/24 AA, 660.02, 660.03, 128/661.08, 691–693, 399; 606/27, 31

[56] References Cited

U.S. PATENT DOCUMENTS

| | | | |
|---|---|---|---|
| 4,586,512 | 5/1986 | Do-huu et al. | 128/660.03 |
| 4,658,828 | 4/1987 | Dory | 128/399 |
| 4,757,820 | 7/1988 | Itoh | 128/660.03 |
| 4,785,823 | 11/1988 | Eggers et al. | 128/692 |
| 4,875,487 | 10/1989 | Seppi | 128/660.03 |
| 4,932,414 | 6/1990 | Coleman et al. | 128/660.09 |
| 4,986,275 | 1/1991 | Ishida et al. | 128/660.03 |
| 5,080,102 | 1/1992 | Dory | 128/660.03 |

OTHER PUBLICATIONS

Shabbo et al., "Thermography in assessing coronary artery saphenous graft patency" *Cardiovascular Res.*, 1982, 158–162.
Rubin et al., "Visualization of Tumor Vascularity in a Rabbit . . . " *J. Ultrasound Med.*, 1987, vol. 6, 113–120.
Cosgrove et al., "Color Doppler Signals From Breast Tumors" *Radiology*, 1990, vol. 6, 175–180.
Adler et al., "Doppler Ultrasound Color Flow Imaging . . . " *Ultrasound in Med. & Biol.*, 1990, vol. 16, No. 6, 553–559.
Hetzel, "Biologic Rationale for Hyperthermia", Radiologic *Clinics of North America*, 1989, v. 27, No. 3, 499–508.
Miller, "Biological Consequences of Hyperthermia," *Ultrasound in Med. & Biol.*, 1989, vol. 15, No. 8, pp. 707–722.

*Primary Examiner*—Lee S. Cohen
*Assistant Examiner*—Kevin Pontius
*Attorney, Agent, or Firm*—W. Brinton Yorks, Jr.

[57] ABSTRACT

A method for accentuating the differences in blood perfusion between normal and tumorous tissue is provided which comprises the steps of measuring the blood perfusion in a local area of the body, heating the local area, then measuring the blood perfusion for variations or inhomogeneities in blood perfusion after the local area has been subjected to heating. As a result of heating normal tissue will generally exhibit increased blood perfusion compared with its preheated condition and as compared with blood perfusion in tumorous tissue, rendering the tumorous tissue more susceptible to detection by techniques such as ultrasonic Doppler blood flow measurement. Apparatus for performing the inventive method is described, including an ultrasonic scanhead which includes a high intensity transducer for heating tissue to be scanned, and an array transducer for performing Doppler measurements of the tissue before and after it has been heated.

9 Claims, 3 Drawing Sheets

DETECTION OF TISSUE ABNORMALITY THROUGH BLOOD PERFUSION DIFFERENTIATION

This invention relates to the detection of tissue abnormalities and, in particular, to the noninvasive detection of tissue abnormalities by measurement of blood perfusion differentiation between normal and abnormal tissue.

Various medical monitoring and diagnostic techniques such as oximetry, angiography, magnetic resonance imaging, and ultrasonic imaging and Doppler measurement are capable of measuring or detecting various characteristics of blood flow. These characteristics are frequently of interest because of the indicia they may provide as to disease states of the body. As one example, it has been suggested that the vasculature of tumors is a particular differentiating feature of tumors. Angiographic studies have demonstrated an abnormal vascularity associated with malignancies that is absent in benign neoplasms. The rapid growth of tumors and their vasculature results in a chaotic structure of the vessels with characteristics such as arteriovenous shunts and localized, high peak velocity flow within the vessels. As a consequence of this phenomenon several studies have been reported on the use of Doppler ultrasound to detect the presence of breast tumors by sensing this abnormally high peak velocity. The Doppler implementation known as color flow Doppler has been recognized as a potentially effective method to detect tumors by sensing flow characteristics of the abnormal vasculature of tumors.

However, the results of the studies have not been encouraging due to inconclusive outcomes of the detection procedure. In one study, high velocity blood flow was observed in 4 cases among 21 patients with breast carcinoma, and one was observed among 33 patients with benign lesions. Hence, the problem is not that false positive results are obtained, but that the high velocity flow condition is not sufficiently great enough to be distinctly discerned from normal flow.

One attempt to address these ambiguous outcomes was the 1987 study by J. M. Rubin et al. entitled "Visualization of tumor vascularity in a rabbit VX2 carcinoma by Doppler flow mapping." In this study Rubin et al. suggested that tumor detection could be enhanced by subjecting the patient to pharmacologically induced changes in vasoconstriction, either those that are naturally induced (e.g., inducing the body's production of adrenaline) or those that are artificially induced (e.g., injecting pharmacological agents.) Doppler measurements made prior to and after application of the pharmacological agent were then compared. This approach, the authors observed, could enhance the tissue classification process. Accordingly, medical researchers are pursuing possible techniques for resolving the ambiguities of this promising technique for tumor detection.

In accordance with the principles of the present invention, a method and apparatus for accentuating the differentiation in blood perfusion between normal and tumorous tissues, then detecting such differentiation, is described. The method comprises the steps of measuring the blood perfusion in the local region being examined, changing the thermal environment of the local region, then measuring the blood perfusion of the local region once more to detect variations or inhomogeneities therein. A preferred technique for changing the thermal environment is to heat the tissue in a manner which is compatible with the measurement modality; for instance, when blood perfusion is being measured by ultrasonic Doppler, ultrasonic heating would be preferred. However, as the following examples will show, any localized heating technique such as microwave heating or heated saline flow may also be employed. The thermal change applied to the localized region should preferably be sufficient enough to cause the desired effect, but be insufficient to cause any damage to healthy tissue.

Also, the measurement modality employed may be selected by the user. While the following examples illustrate the use of color flow Doppler, other techniques for measuring blood perfusion such as magnetic reasonance imaging may also be employed.

Figure 1:
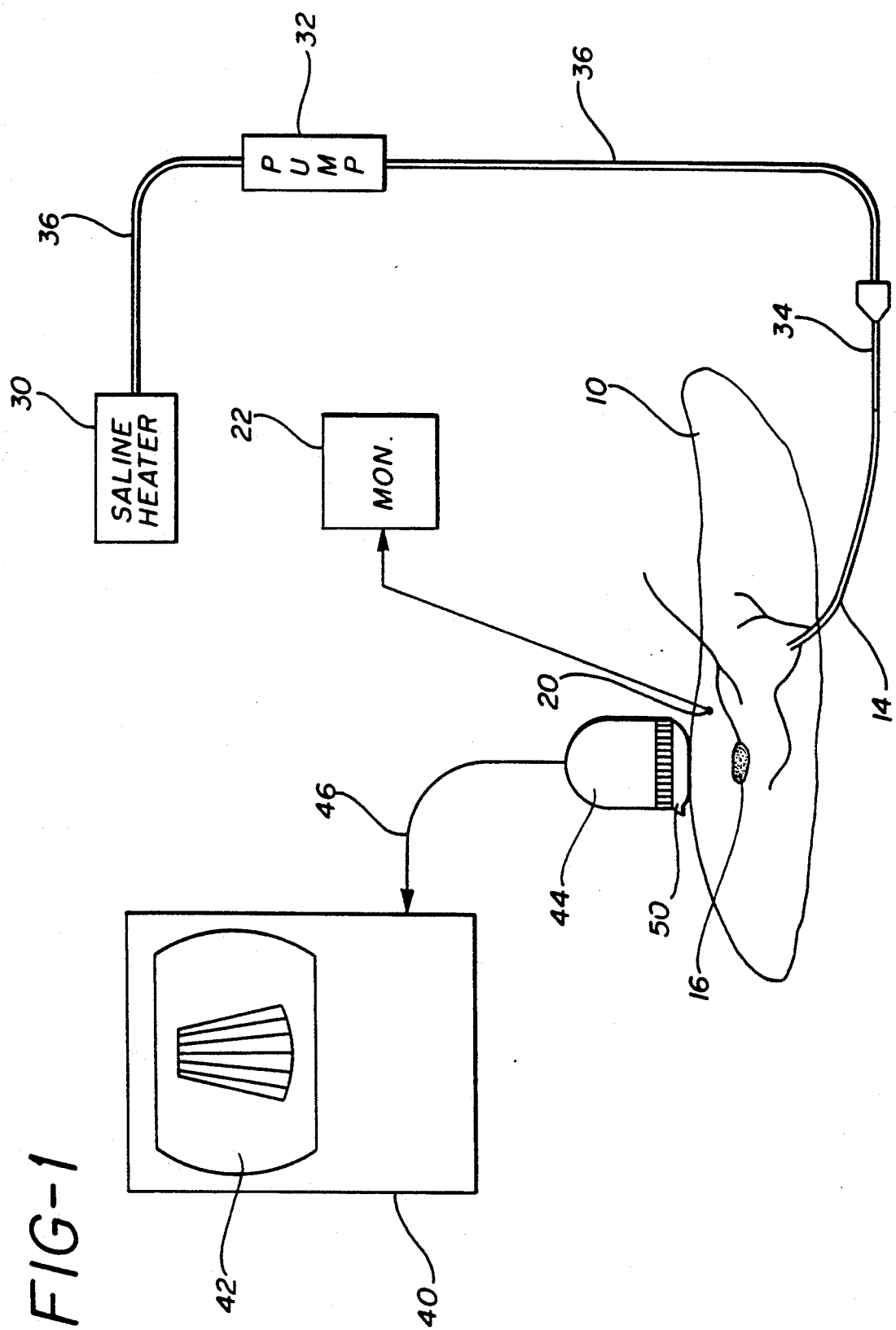
FIG. 1 illustrates apparatus for performing the method of the present invention while examining a liver for tumors.

Referring first to FIG. 1, apparatus for performing the method of the present invention when examining a liver for tumors is shown. In the drawing a liver 10 is shown containing a tumor 16. The area of the tumor is to be warmed with heated saline solution to better differentiate the blood perfusion of the tumor as compared to that of the surrounding normal tissue when the area of the tumor is scanned ultrasonically. The saline solution is to be supplied through the portal vein 14 which is cannulated with an intravenous catheter 34. Saline solution from a saline heater 30 is supplied to the catheter by an infusion pump 32 and tubing 36.

In the practice of the procedure of the present invention the liver may first be surveyed by ultrasonic scanning to determine the presence of any tumors or to identify any regions where the presence of a tumor is suspected. The survey scan will also establish a baseline against which any changes in blood perfusion may be gauged. The scanning may be performed using a phased array scanhead 44 connected to a scanning system 40 for the production of a color Doppler image 42 depicting blood flow velocity. One such suitable arrangement is an Ultramark 9 scanning system produced by Advanced Technology Laboratories and using a 45 mm aperture, 5 MHz array transducer. To increase the aperture just beneath the surface of the liver, an acoustic stand-off pad 50 is used.

After the survey scan is performed, heated saline solution is pumped into the portal vein to warm the liver. The saline is heated to a temperature in excess of normal body temperature so that the liver will be warmed to the range of 39° C. to 41° C. The body temperature in the area being warmed is monitored by a thermistor 20 inserted into the area being warmed. The monitor 22 provides a reading of body temperature. The saline is pumped into the portal vein at a rate of 0.5 cc/sec. for periods of a minute every three minutes. The liver is then scanned again while at this elevated temperature range in a search for contrasting differences in blood perfusion between healthy and tumorous tissue.

It has been found that blood flow in tumors decreases substantially (by about 50%) as a function of local temperature in the 39° C. to 4° C. range following an initial, small rise. Prolonged temperatures in excess of 43° C. result in the virtual elimination of capillary blood flow in both normal and malignant tissue. Furthermore, it has been determined that thermal tissue damage can occur when tissue is exposed to excessive temperatures for a prolonged period of time, whereby the degree of tissue injury is functionally related to both the temperature and the time of exposure. For example, the application of temperatures in excess of 45° C. for more than one minute can result in thermal tissue damage. Hence, the heated saline solution is applied at a rate and a periodicity so as to maintain the elevated temperature of the liver in the range of 39° C. to 41° C. As the liver is scanned while the temperature is rising to the elevated level, the differentiation in flow between the tumorous and normal tissue will increase as the blood flow in the tumor decreases. Differentiation in flow which is within the range of Doppler sensitivity will become evident in the color Doppler image of blood flow in the vascular structure, allowing the tumor to be visually detected in the image. The differentiation is generally greatest at the periphery of the tumor, the interface between the vasculature of the tumor and that of the surrounding healthy tissue.

Figure 2:
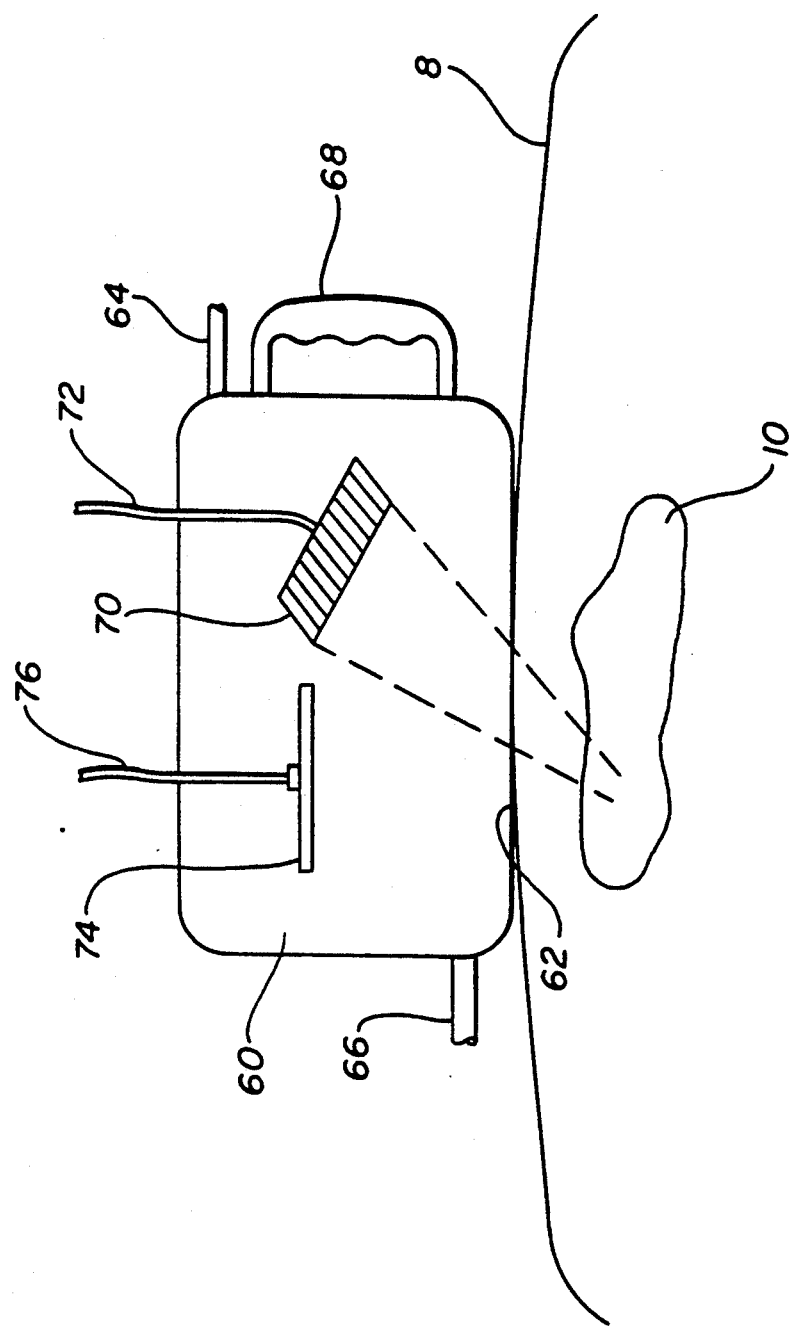
FIG. 2 illustrates an ultrasonic imaging and heating scanhead used to perform the method of the present invention.

A second method of changing the local thermal environment of tissue being examined in accordance with the present invention is illustrated in FIG. 2. This figure shows an ultrasonic scanhead 60 which contains a high intensity transducer 74 which performs ultrasonic heating of a local area of the subject 8, and a phased array imaging transducer 70 for scanning the local area after it has been heated. The two transducers of the scanhead are enclosed within a water filled housing 78 and are both directed toward a mass 10 within the subject 8 which is to be diagnosed. The scanhead can be held and manipulated by means of a handle 68. Water flows into the housing 78 through an inlet port 64, and exits the housing by way of an outlet port 66. Water is pumped through the housing when the high intensity transducer is heating the subject to prevent spot heating, the buildup of heat at any given point within the housing. The water also provides a suitable acoustic medium for the transmission of ultrasonic energy through the scanhead. The ultrasonic energy from the two transducers, as well as echo information returning to the imaging transducer, passes through an acoustic window 62 which contacts the subject 8. A layer of coupling gel is used to couple ultrasonic energy between the membrane of the acoustic window and the subject to avoid spot heating at the skin surface.

The high intensity transducer 74 may be a single piston or array transducer. In the present embodiment the transducer is unfocused to transmit a uniformly distributed beam of energy into the subject. The transducer 74 is energized by a continuous wave signal having a frequency determined by the desired tissue depth at which heating is to occur. Since lower frequencies penetrate deeper into tissue than higher frequencies (which are absorbed faster near the surface), an acceptable frequency of operation for a transducer for heating at depths to 2 cm is 3 MHz, and a frequency for heating down to a 10 cm depth is 0.5 MHz. A transducer with a nominal frequency of 2.0 MHz would be acceptable for heating in a depth range of 1 to 3 cm, for instance. The frequency of operation of the diagnosing array transducer 70 would likewise be chosen in consideration of penetration depths.

Figure 3:
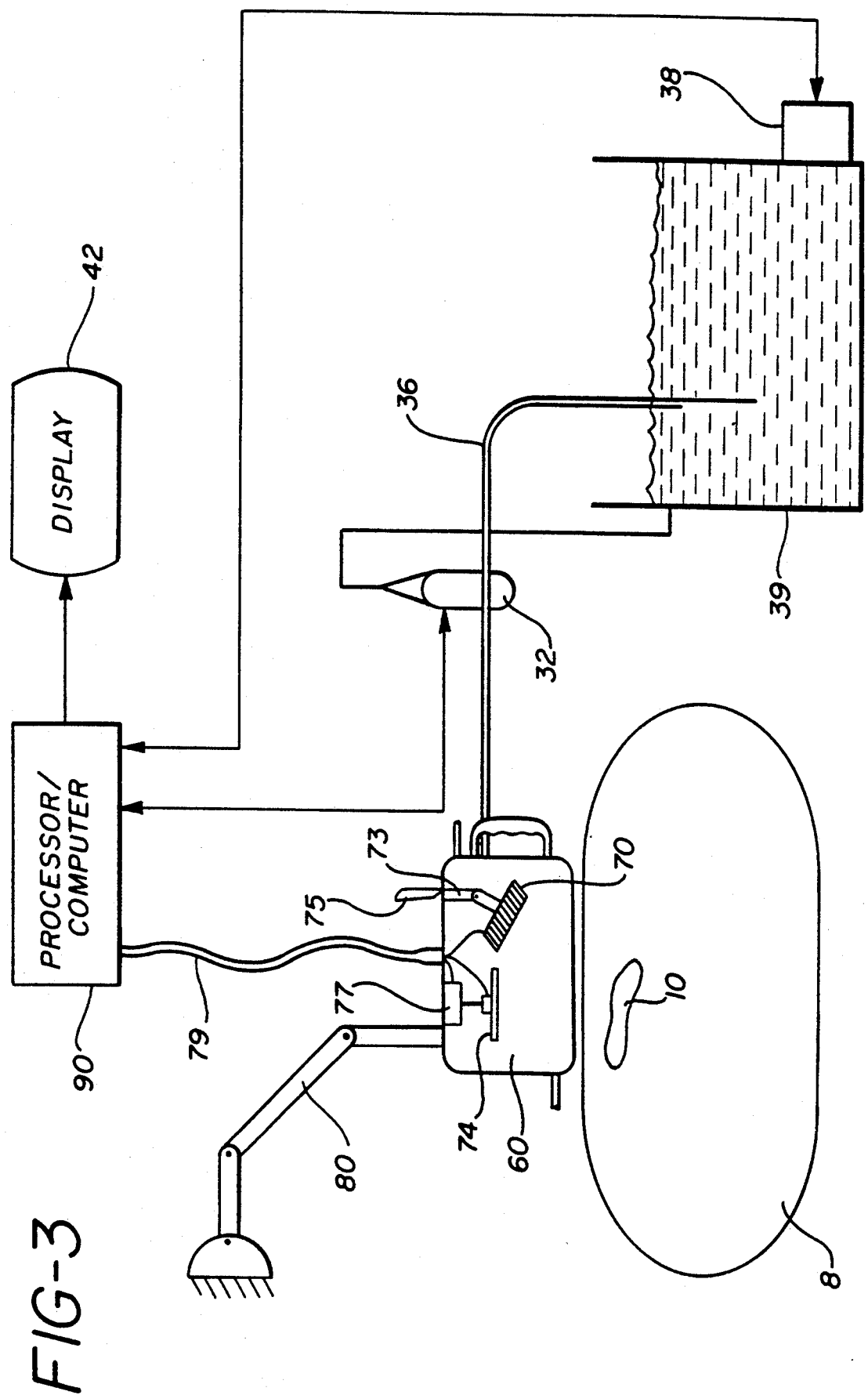
FIG. 3 illustrates an ultrasonic system for performing the method of the present invention using the scanhead of FIG. 2.

In the system configuration of FIG. 3, the high intensity transducer 74 is mounted on the shaft of a motor 77 in the housing 78. The motor rotates the transducer while it is transmitting to dissipate heat from any hot spots on the surface of the transducer, and also to mechanically smooth the heating effect. The motor and transducers 70 and 74 are controlled and energized by leads of a cable 79 from a processor/computer 90. FIG. 3 also shows the array transducer 70 mounted on a mechanical steering mechanism 73, controlled by a handle 75 on the exterior of the housing 78. The steering mechanism enables the array transducer to be directed at, and hence scan, the local area beneath the heating transducer 74 at the depth where the tissue is to be examined for tumor evidence.

To facilitate support of the scanhead while in use, whereby the scanhead can be maintained in a fixed position during use but still be moved and positioned readily, the scanhead 60 is supported by an articulating support 80. While the end of the support 80 remote from the scanhead is indicated as attached to a fixed surface in the drawing, it could as well be attached to a mobile cart or similar mechanism.

Tubing lines 36 are connected between the water inlet and outlet ports 64 and 66 of the scanhead 60 and a water tank 39. The water is pumped through the scanhead by an infusion pump 32 which is actuated and controlled by processor/computer 90. Generally the pump 32 will begin pumping at the same time that the processor/computer actuates the high intensity transducer 74 and motor 77 to heat the local area being investigated. The pump is stopped a short time after the high intensity transducer 74 is turned off by the procesor/computer. The water in the water tank 39 is warmed to a temperature near body temperature by a heater 38 for patient comfort. Warming of the water may be thermistatically controlled or under control of the processor/computer 90. In addition, the processor/computer may monitor the water level in the tank.

The data and image information gathered by the array transducer 70 is processed by the processor/computer as is customary for ultrasound data and the results are displayed on a display 42.

The power level at which the high intensity transducer is operated, as well as the durations for which it is energized, are controlled in relation to each other by the processor/controller so as to automatically maintain a margin of patient safety. For instance, normal tissue withstand insonification at a power intensity of 100 watts/cm² for a period of five minutes without sustaining injury. Also, normal tissue can withstand 400 watts/cm² of insonification for five seconds without sustaining injury. The relation which governs this measure of safe insonification levels is $$\Delta T = \frac{2\alpha I}{\rho c J} \Delta t \qquad (1)$$

where $\Delta T$ is temperature rise, $\alpha$ is a pressure absorpton coefficient in $cm^{-1}$, I is acoustic intensity in watts/cm², $\rho c$ is heat capacity per unit volume in calories per cm³, J is the mechanical equivalent of heat in Joules/calorie, and $\Delta t$ is irradiation time in seconds. The processor/computer solves this equation for one of its variables, irradiation time, temperature rise, or acoustic intensity in response to input of the others, and checks all results against predetermined limits for patient safety. For instance, if the clinician desired to heat the body 4°·C. in four seconds, calculation of the formula would yield a required acoustic power intensity of 67 watts/cm². This result is then used in the expression $$\frac{V^2}{R} = I \times A \quad (2)$$

where V is the transducer drive voltage, R is the impedance of the high intensity transducer in ohms, and A is the radiating surface area of the transducer in cm². For a 10 ohm, 100 cm² transducer to deliver an acoustic power intensity of 67 watts/cm² for instance the energizing voltage must be approximately 260 volts rms. The processor/controller would therefore drive the high intensity transducer with a 260 volt signal for 4 seconds in this example.

The foregoing computations and control criteria are used to determine the power density delivered at the acoustic window 62, which is normally at the skin surface. Not taken into consideration in equation (1) are bodily effects of axial and lateral thermal conduction and thermal dissipation through blood perfusion, both of which provide a further margin of safety when heating the body as described above.

In use of the system of FIG. 3, the clinician would first survey the local area in the body where tumors may be suspected. The scanhead is positioned over the body with the area to be interrogated located beneath the high intensity transducer 74. The steering mechanism 73 is then manipulated to scan the body at the desired depth. Normal (i.e., in the absence of temperature elevation) perfusion characteristics are measured by the transducer 70, processed by the processor/computer 90, and the results displayed on the display 42. A color flow map of the area in question may be presented, for instance.

The clinician next decides the temperature rise to apply and the time period over which heating is to occur. The computer/processor checks the input of these data values against safety limits and, if they are acceptable, the computer/processor calculates the acoustic intensity using equation (1). The drive voltage is then determined using equation (2) and the high intensity transducer, pump and motor are energized to heat the area being interrogated. During and subsequent to the heating the local area is scanned to measure and detect perfusion effects indicative of tumors, as enhanced by the local area heating. The enhanced perfusion effect measurements, such as a color flow map of the local area, are displayed on the display 42. The clinician may compare the pre- and post-heating perfusion to determine whether a tumor is indicated.

In addition to determining that the parameters of temperature rise to be used in the procedure are within proper limits, the computer/processor 90 can store predetermined values of temperature rise and heating times which are specific for various organs. These values could be determined for instance from previous procedures and empirical research in use of the present technique for tumor detection. Also, the computer/processor can be programmed to control retriggering, that is, the recovery time which is allowed to pass after the performance of one procedure before the procedure is again performed on the same local area.

Other apparatus can be used to perform the inventive technique of enhanced tumor detection for specific areas of the body. For instance in the examination of the prostate gland for the presence of tumors, heat could be applied by a small microwave antenna introduced by a catheter through the urethra to the vicinity of the prostate gland. Color flow imaging of the effects on blood perfusion of heating can be determined by a trans-rectal ultrasonic transducer such as the TRT Biplane Sector/Linear probe manufactured by Advanced Technology Laboratories and suitable for use with the Ultramark 9 ultrasonic imaging system.

What is claimed is:

1. A method for accentuating differences in blood perfusion between normal and tumorous tissue by means of an applied or induced change in the local thermal environment of a region of normal tissue to be examined which contains tumuous tissue comprising the steps of:
   measuring blood perfusion in said region;
   changing the thermal environment of said region;
   measuring the response of blood perfusion to the thermal change to detect variations or inhomogenieties in blood perfusion of said region;
   wherein the step of changing the thermal environment of said region comprises heating said region; and
   wherein the step of measuring the response of blood perfusion to the thermal change comprises sensing for a decrease in the blood flow of local vasculature as the temperature of said region increases.

2. The method of claim 1, wherein the step of sensing for a decrease in the blood flow of local vasculature comprises monitoring the blood flow of local vasculature by ultrasonic Doppler flow measurement.

3. The method of claim 2, wherein the step of monitoring the blood flow of local vasculature by ultrasonic Doppler flow measurement includes producing a color flow map of said region.

4. The method of claim 1, wherein the step of sensing for a decrease in the blood flow of local vasculature comprises monitoring the blood flow of local vasculature by magnetic resonance imaging.

5. An ultrasonic system for inducing heating of a subject tissue and for measuring differences in blood perfusion resulting therefrom comprising:
   means for measuring blood perfusion in said subject tissue;
   means for changing the thermal environment of said subject tissue by heating by a predetermined amount through the application of ultrasonic energy;
   means for measuring the response of blood perfusion to the thermal change to detect variations or inhomogenieties in blood perfusion of said subject tissue which have been accentuated by heating;
   wherein said means for measuring the response of blood perfusion to the thermal change includes a means for sensing for a decrease in the blood perfusion as the temperature of said subject tissue increases; and
   means for controlling said means for heating said subject tissue and said means for measuring the response of blood perfusion.

6. The ultrasonic system of claim 5, including a scanhead and wherein said means for changing the thermal environment comprises a first transducer means for heating said subject tissue by irradiation with ultrasonic energy, and wherein said means for measuring the response of blood perfusion comprises a second transducer means for ultrasonically detecting differences in blood perfusion in the subject tissue and wherein said first transducer means and said second transducer means are disposed within said scanhead.

7. The ultrasonic system of claim 6, wherein said second transducer means is controlled by said controlling means to measure blood perfusion through ultrasonic Doppler interrogation of the subject tissue.

8. The ultrasonic system of claim 6, wherein said controlling means controls said first transducer means so that the intensity of ultrasonic irradiation and the time of irradiation are below the level at which thermal tissue damage occurs.

9. The ultrasonic system of claim 8, wherein said controlling means controls said first transducer means so that the temperature of the subject tissue irradiated by said first transducer means increases to the range of 39° C. to 41° C.

* * * * *